United States Patent
Kouno et al.

(10) Patent No.: US 8,053,608 B2
(45) Date of Patent: Nov. 8, 2011

(54) PROCESS FOR PRODUCING PROPYLENE GLYCOL

(75) Inventors: Hiroshi Kouno, Ichihara (JP); Shuji Ozawa, Yokohama (JP); Naritoshi Yoshimura, Funabashi (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 0 days.

(21) Appl. No.: 12/740,197

(22) PCT Filed: Oct. 28, 2008

(86) PCT No.: PCT/JP2008/069527
§ 371 (c)(1),
(2), (4) Date: Apr. 28, 2010

(87) PCT Pub. No.: WO2009/057584
PCT Pub. Date: May 7, 2009

(65) Prior Publication Data
US 2010/0256425 A1    Oct. 7, 2010

(30) Foreign Application Priority Data

Oct. 31, 2007  (JP) ................................ 2007-283402
Jun. 13, 2008  (JP) ................................ 2008-155666

(51) Int. Cl.
*C07C 29/60* (2006.01)

(52) U.S. Cl. ........................................................ 568/861
(58) Field of Classification Search ................... 568/861
See application file for complete search history.

(56) References Cited

U.S. PATENT DOCUMENTS

| 4,199,479 A | 4/1980 | Wilkes |
| 4,283,581 A | 8/1981 | Wilkes |
| 5,214,219 A | 5/1993 | Casale et al. |
| 2007/0149830 A1 | 6/2007 | Tuck et al. |

FOREIGN PATENT DOCUMENTS

JP    57-122941    7/1982

OTHER PUBLICATIONS

International Search Report for PCT/JP2008/069527 mailed Dec. 2, 2008.
Wang et al, Catalysis Letters, Sep. 26, 2007, vol. 117, pp. 62-67.
Park et al, Applied Catalysis A: General, 2003, vol. 253, pp. 249-255.

*Primary Examiner* — Sikarl Witherspoon
(74) *Attorney, Agent, or Firm* — Rankin, Hill & Clark LLP

(57) ABSTRACT

It is an object of the present invention to provide a process for producing propylene glycol from glycerol as a raw material without the necessity for a step of gasifying glycerol. The process for producing propylene glycol of the present invention comprises a step of subjecting glycerol to catalytic hydrogenation in the presence of a catalyst A containing zinc oxide, silica, and at least one of copper and copper oxide.

20 Claims, No Drawings

PROCESS FOR PRODUCING PROPYLENE GLYCOL

TECHNICAL FIELD

The present invention relates to a process for producing propylene glycol from glycerol as a raw material.

BACKGROUND ART

As one of the measures to suppress global warming, fuels for diesel engines which are called biodiesel and are produced from fats of plants and/or animals serving as raw materials have recently been developed. In a production process of biodiesel, glycerol is produced as a by-product in an amount of about 10% with respect to the raw-material fats. The effective utilization of the glycerol has been intensively investigated.

Meanwhile, propylene glycol is a compound in which a hydroxyl group at the 1-position of glycerol is converted into hydrogen. Propylene glycol has low toxicity to animate beings and is tasteless and odorless, because of which it is widely used as a humectant, a lubricant, an emulsifier, anti-freeze, solvent or the like, in the fields of pharmaceuticals, cosmetics, food and so forth. Generally, propylene glycol is produced by oxidizing propylene derived from petroleum called fossil materials to prepare propylene oxide, followed by hydration.

Here, regarding the effective utilization of the glycerol, it is known that glycerol is converted into propylene glycol with a copper catalyst. For example, U.S. Pat. No. 5,214,219 specification discloses a process for converting glycerol into propylene glycol and ethylene glycol by reacting glycerol with hydrogen in the presence of a catalyst containing copper oxide and zinc oxide.

Furthermore, WO2007/010299 pamphlet discloses a process for hydrogenating glycerol in the presence of a catalyst at a specific reaction temperature and a specific reaction pressure, with specific amount ratio of hydrogen to raw materials and for a specific reaction time in a gaseous phase. A catalyst containing copper oxide and zinc oxide, a catalyst containing copper oxide and silica, and the like are exemplified as the catalyst used for the reaction. According to the process, although propylene glycol can be produced in a high yield and at a high conversion of glycerol, glycerol needs to be vaporized with a vaporizer. This results in an increase in energy necessary for performing the reaction and is economically disadvantageous, which requires improvement.

As described above, various processes for producing propylene glycol have been developed by focusing attention on catalysts and reaction conditions. However, the foregoing patent documents are silent on a catalyst containing all of copper oxide, zinc oxide and silica and provides no disclosure or suggestion on the appropriate proportions thereof and the like.

[Patent Document 1] U.S. Pat. No. 5,214,219 specification
[Patent Document 2] WO2007/010299 pamphlet

DISCLOSURE OF INVENTION

Problems to be Solved by the Invention

It is an object of the present invention to provide a process for producing propylene glycol from glycerol as a raw material without necessity for a step of vaporizing glycerol.

Means for Solving the Problems

The present inventors have conducted intensive studies to overcome the foregoing problems and have found that the problems are solved by the use of a catalyst containing zinc oxide, silica, and at least one of copper and copper oxide to complete the present invention. In particular, the present inventors have found that by the use of a catalyst containing the three components in a specific proportion, propylene glycol can be produced in a high yield. Furthermore, the present inventors have found that the preferred proportions of the components in the catalyst vary depending on a method for preparing the catalyst.

That is, the gist of the present invention is a process for producing propylene glycol comprising a step of subjecting glycerol to catalytic hydrogenation in the presence of a catalyst A containing zinc oxide, silica, and at least one of copper and copper oxide.

The catalyst A preferably has a silica content of 0.1% to 25% by weight with respect to 100% by weight of the catalyst A.

The weight ratio of the at least one of copper and copper oxide to silica (at least one of copper and copper oxide:silica) in the catalyst A is preferably in the range of 0.5:1 to 700:1.

Furthermore, it is also preferable that the weight ratio of the at least one of copper and copper oxide to zinc oxide (at least one of copper and copper oxide:zinc oxide) in the catalyst A is in the range of 6:1 to 5:90.

In the case where the catalyst A is prepared by a coprecipitation method or an impregnation method, the catalyst A preferably has a silica content of 0.1% to 25% by weight with respect to 100% by weight of the catalyst A. The weight ratio of the at least one of copper and copper oxide to silica (at least one of copper and copper oxide:silica) in the catalyst A is preferably in the range of 0.5:1 to 700:1. The weight ratio of the at least one of copper and copper oxide to zinc oxide (at least one of copper and copper oxide:zinc oxide) in the catalyst A is preferably in the range of 6:1 to 5:90.

Further, in the case where the catalyst A is prepared by mixing silica and a catalyst containing zinc oxide and at least one of copper and copper oxide, the catalyst A preferably has a silica content of 0.1% to 4.5% by weight with respect to 100% by weight of the catalyst A. The weight ratio of the at least one of copper and copper oxide to silica (at least one of copper and copper oxide:silica) in the catalyst A is preferably in the range of 1.5:1 to 700:1. The weight ratio of the at least one of copper and copper oxide to zinc oxide (at least one of copper and copper oxide:zinc oxide) in the catalyst A is preferably in the range of 6:1 to 5:90.

In the case where the catalyst A is prepared by mixing a catalyst containing zinc oxide and at least one of copper and copper oxide and a silica-containing substance or a silica-containing catalyst, the catalyst A preferably has a silica content of 0.1% to 10% by weight with respect to 100% by weight of the catalyst A. The weight ratio of the at least one of copper and copper oxide to silica (at least one of copper and copper oxide:silica) in the catalyst A is preferably in the range of 5:1 to 700:1. The weight ratio of the at least one of copper and copper oxide to zinc oxide (at least one of copper and copper oxide:zinc oxide) in the catalyst A is preferably in the range of 6:1 to 5:90.

On the other hand, in the case where the catalyst A is prepared by extrusion molding of a catalyst containing zinc oxide and at least one of copper and copper oxide or a catalyst containing zinc oxide, silica and at least one of copper and copper oxide, and a silica-containing inorganic binder, the catalyst A preferably has a silica content of 0.1% to 25% by weight with respect to 100% by weight of the catalyst A. The weight ratio of the at least one of copper and copper oxide to silica (at least one of copper and copper oxide:silica) in the catalyst A is preferably in the range of 1.2:1 to 700:1. The weight ratio of the at least one of copper and copper oxide to zinc oxide (at least one of copper and copper oxide:zinc oxide) in the catalyst A is preferably in the range of 6:1 to 5:90.

Advantages of the Invention

According to the present invention, the use of the catalyst A containing zinc oxide, silica and at least one of copper and copper oxide permits the production of propylene glycol from glycerol without vaporization of glycerol. Furthermore, by the use of the catalyst containing the three components in a specific proportion, propylene glycol can be produced in a high yield. Thus, the production process of the present invention has a high utility value in industry.

BEST MODE FOR CARRYING OUT THE INVENTION

A process for producing propylene glycol using a specific catalyst of the present invention will be described in detail below.

[Catalyst A Containing Zinc Oxide, Silica and at Least One of Copper and Copper Oxide]

A catalyst used in the present invention is a catalyst A that contains zinc oxide, silica and at least one of copper and copper oxide. A method for preparing it is not particularly limited. Examples thereof include:
(1) a method in which it is prepared by a coprecipitation method or an impregnation method with various types of salts of copper, zinc and silicon as raw materials;
(2) a method in which a catalyst containing zinc oxide and at least one of copper and copper oxide is mixed with silica;
(3) a method in which a catalyst containing zinc oxide and at least one of copper and copper oxide is mixed with a silica-containing substance or a silica-containing catalyst; and;
(4) a method in which a catalyst containing zinc oxide and at least one of copper and copper oxide or a catalyst containing zinc oxide, silica and at least one of copper and copper oxide and
a silica-containing inorganic binder are subjected to extrusion molding.

The catalyst A can be prepared by, for example, the methods described above. The present inventors found that preferred proportion of zinc oxide, silica and at least one of copper and copper oxide in the catalyst A varied depending on how the catalyst A was prepared. Catalysts prepared by the four methods described above will be described below.

<Catalyst Prepared by Method (1)>

In the method (1) described above, a catalyst is prepared by a known method, e.g., a coprecipitation method or an impregnation method, with
at least one selected from the group consisting of nitrate, sulfate, carbonate, acetate, chloride, oxide, hydroxide and the like of copper,
at least one selected from the group consisting of nitrate, sulfate, carbonate, acetate, chloride, oxide, hydroxide and the like of zinc, and
at least one selected from the group consisting of silica, colloidal silica, sodium silicate and the like as raw materials.

For example, in a method called the coprecipitation method, an aqueous solution containing copper nitrate, zinc nitrate and sodium silicate is reacted in the presence of a base to form a coprecipitate that contains copper, zinc and silicon. The coprecipitate is dried and calcined to yield the catalyst used in the present invention. The calcination is usually performed at 300° C. to 600° C. for 1 to 6 hours.

The content proportion of zinc oxide, silica and at least one of copper and copper oxide in the catalyst prepared by the method (1) can be adjusted by changing the amount proportion of at least one selected from the group consisting of nitrate, sulfate, carbonate, acetate, chloride, oxide, hydroxide and the like of copper used,
at least one selected from the group consisting of nitrate, sulfate, carbonate, acetate, chloride, oxide, hydroxide and the like of zinc used, and
at least one selected from the group consisting of silica, colloidal silica, sodium silicate and so forth.

The catalyst prepared by the method (1) preferably has a silica content of 0.1% to 25% by weight, more preferably 0.1% to 20% by weight, and particularly preferably 0.5% to 15% by weight with respect to 100% by weight of the catalyst. The yield of propylene glycol when produced using the catalyst significantly varies depending on whether the silica content is within the above range or not. The use of the catalyst having a silica content within the above range permits producing propylene glycol in extremely high yield as compared with the case of using a catalyst having a silica content outside the above range.

The weight ratio of at least one of copper and copper oxide to silica (at least one of copper and copper oxide:silica) contained in the catalyst prepared by the method (1) is preferably in the range of 0.5:1 to 700:1, more preferably 1:1 to 500:1, and more preferably 1.5:1 to 100:1. The yield of propylene glycol when produced using the catalyst significantly varies depending on whether the weight ratio is within the above range or not. The use of the catalyst having a weight ratio within the above range permits producing propylene glycol in extremely high yield as compared with the case of using a catalyst having a weight ratio outside the above range.

The weight ratio of at least one of copper and copper oxide to zinc oxide (at least one of copper and copper oxide:zinc oxide) contained in the catalyst prepared by the method (1) is not particularly limited, but it is usually in the range of 6:1 to 5:90, preferably 5:1 to 10:90, more preferably 3:1 to 6:35, and particularly preferably 2:1 to 6:35. The use of the catalyst having a weight ratio within the above range allows a catalytic reaction to proceed with a high yield.

The catalyst prepared by the method (1) may contain a fourth component other than copper oxide, zinc oxide and silica to the extent that the present reaction (reaction to prepare propylene glycol by catalytic hydrogenation of glycerol) is not inhibited.

Examples of the component include alkali metals such as sodium, potassium and cesium; alkaline-earth metals such as magnesium and barium; transition metals such as zirconium, manganese, iron, nickel, cobalt, chromium, rhodium, ruthenium, palladium and platinum; the periodic table group 13 elements such as aluminum; and oxides thereof.

The incorporation of the fourth component into the catalyst is expected to improve the persistence of the effect of the catalyst and the stability of the catalyst.

<Catalyst Prepared by Method (2)>

In the method (2), a catalyst 1 containing zinc oxide and at least one of copper and copper oxide is mixed with silica to prepare a catalyst. The mixing is physical mixing.

A catalyst prepared by the foregoing known method (e.g., the coprecipitation method, the impregnation method or a kneading method) and those commercially available (e.g., F10G manufactured by Nikki Chemical Co., Ltd. or ShiftMax 210 manufactured by Sud-Chemie catalysts Japan, Inc.) may be used as the catalyst 1 used in the method (2).

Examples of silica that can be used include silica prepared by a known method, for example, hydrothermal synthesis;

and commercially available silica (e.g., CARiACT Q6, manufactured by Fuji Silysia Chemical Ltd.).

The catalyst prepared by the method (2) preferably has a silica content of 0.1% to 4.5% by weight, more preferably 0.1% to 4% by weight, and particularly preferably 0.2% to 4% by weight with respect to 100% by weight of the catalyst. The yield of propylene glycol when produced using the catalyst significantly varies depending on whether the silica content is within the above range or not. The use of the catalyst having a silica content within the above range permits producing propylene glycol in extremely high yield as compared with the case of using a catalyst having a silica content outside the above range.

By adjusting the ratio of the powder of catalyst 1 to the powder of silica mixed and the ratio of the at least one of copper and copper oxide to zinc oxide in the catalyst 1 when the catalyst is prepared by the method (2), the proportion of zinc oxide, silica and the at least one of copper and copper oxide in the resulting catalyst can be adjusted.

The weight ratio of at least one of copper and copper oxide to silica (at least one of copper and copper oxide:silica) contained in the catalyst prepared by the method (2) is preferably in the range of 1.5:1 to 700:1, more preferably 2.5:1 to 650:1, particularly preferably 5:1 to 350:1. The yield of propylene glycol when produced using the catalyst significantly varies depending on whether the weight ratio is within the above range or not. The use of the catalyst having a weight ratio within the above range permits producing propylene glycol in extremely high yield as compared with the case of using a catalyst having a weight ratio outside the above range.

The weight ratio of at least one of copper and copper oxide to zinc oxide (at least one of copper and copper oxide:zinc oxide) contained in the catalyst prepared by the method (2) is not particularly limited, but it is usually 6:1 to 5:90, preferably 5:1 to 10:90, more preferably 3:1 to 6:35, and particularly preferably 2:1 to 6:35. The use of the catalyst having a weight ratio within the above range allows a catalytic reaction to proceed with a high yield.

The catalyst prepared by the method (2) may contain a fourth component other than zinc oxide, silica and at least one of copper and copper oxide to the extent that the present reaction is not inhibited.

Examples of the component include alkali metals such as sodium, potassium and cesium; alkaline-earth metals such as magnesium and barium; transition metals such as zirconium, manganese, iron, nickel, cobalt, chromium, rhodium, ruthenium, palladium and platinum; the periodic table group 13 elements such as aluminum; and oxides thereof.

The incorporation of the fourth component into the catalyst is expected to improve the persistence of the effect of the catalyst and the stability of the catalyst.

The fourth component may be appropriately contained in the catalyst 1 and/or silica. That is, it may be contained in one or both of the catalyst 1 and silica.

<Catalyst Prepared by Method (3)>

In the method (3), a catalyst 2 containing zinc oxide and at least one of copper and copper oxide is mixed with a silica-containing substance or a silica-containing catalyst. The mixing is physical mixing.

The same catalyst as the catalyst 1 which contains zinc oxide and at least one of copper and copper oxide and is explained as to the catalyst prepared by the method (2) described above is exemplified as the catalyst 2.

Examples of the silica-containing substance or silica-containing catalyst include known composite oxides such as silica/alumina and silica/magnesia (these do not have catalytic activity); and catalysts containing silica and at least one of copper and copper oxide.

Examples of the catalyst containing silica and at least one of copper and copper oxide include a catalyst containing silica and at least one of copper and copper oxide produced by the known method (the coprecipitation method, the impregnation method, the kneading method or the like); and those commercially available (e.g., E35S manufactured by Nikki Chemical Co., Ltd., KC-1H manufactured by Sakai Chemical Industry Co., Ltd., and Cu-0860E manufactured by N.E. CHEMCAT Corporation).

The catalyst prepared by the method (3) preferably has a silica content of 0.1% to 10%, more preferably 0.1% to 9% by weight, and particularly preferably 0.5% to 6% by weight with respect to 100% by weight of the catalyst. The yield of propylene glycol when produced using the catalyst significantly varies depending on whether the silica content is within the above range or not. The use of the catalyst having a silica content within the above range permits producing propylene glycol in extremely high yield as compared with the case of using a catalyst having a silica content outside the above range.

The content proportion of zinc oxide, silica and the at least one of copper and copper oxide in the catalyst obtained by the method (3) can be adjusted by adjusting the following ratios during the preparation of the catalyst:

(i) the amount ratio of the powder of the catalyst 2 to the powder of the silica-containing substance or the silica-containing catalyst mixed;

(ii) the amount ratio of the at least one of copper and copper oxide to zinc oxide in the catalyst 2; and (iii) in the case where the silica-containing substance or silica-containing catalyst contains zinc oxide or at least one of copper and copper oxide, the amount ratio of silica to at least one of copper and copper oxide and/or zinc oxide in the silica-containing substance or silica-containing catalyst.

The weight ratio of the at least one of copper and copper oxide to silica (at least one of copper and copper oxide:silica) contained in the catalyst prepared by the method (3) is preferably in the range of 5:1 to 700:1, more preferably 5:1 to 500:1, and particularly preferably 8:1 to 100:1. The yield of propylene glycol when produced using the catalyst significantly varies depending on whether the weight ratio is within the above range or not. The use of the catalyst having a weight ratio within the above range permits producing propylene glycol in extremely high yield as compared with the case of using a catalyst having a weight ratio outside the above range. Here, when the silica-containing substance or silica-containing catalyst contains at least one of copper and copper oxide, the weight of the at least one of copper and copper oxide means the sum of the weights of copper and copper oxide in the catalyst 2 and the weights of copper and copper oxide in the silica-containing substance or silica-containing catalyst.

The weight ratio of at least one of copper and copper oxide to zinc oxide (at least one of copper and copper oxide:zinc oxide) contained in the catalyst prepared by the method (3) is not particularly limited, but it is usually in the range of 6:1 to 5:90, preferably 5:1 to 10:90, more preferably 3:1 to 6:35, and particularly preferably 2:1 to 6:35. The use of the catalyst having a weight ratio within the above range allows a catalytic reaction to proceed with a high yield. Here, when the silica-containing substance or silica-containing catalyst contains at least one of copper and copper oxide, the weight of the at least one of copper and copper oxide means the sum of the weights of copper and copper oxide in the catalyst 2 and the weights of copper and copper oxide in the silica-containing substance or silica-containing catalyst. Further, when the silica-containing substance or silica-containing catalyst contains zinc oxide, the weight of zinc oxide means the sum of the weight of zinc oxide in the catalyst 2 and the weight of zinc oxide in the silica-containing substance or silica-containing catalyst.

The catalyst prepared by the method (3) may contain a fourth component other than zinc oxide, silica and at least one of copper and copper oxide to the extent that the present reaction is not inhibited.

Examples of the component include alkali metals such as sodium, potassium and cesium; alkaline-earth metals such as magnesium and barium; transition metals such as zirconium, manganese, iron, nickel, cobalt, chromium, rhodium, ruthenium, palladium, and platinum; the periodic table group 13 elements such as aluminum; and oxides thereof.

The incorporation of the fourth component into the catalyst is expected to improve the persistence of the effect of the catalyst and the stability of the catalyst.

The fourth component may be appropriately contained in the catalyst 2 and/or the silica-containing substance or silica-containing catalyst. That is, the fourth component may be contained in one or both of the catalyst 2 and the silica-containing substance or silica-containing catalyst.

<Catalyst Prepared by Method (4)>

In the method (4) described above, a catalyst 3 containing zinc oxide and at least one of copper and copper oxide or a catalyst 4 containing zinc oxide, silica and at least one of copper and copper oxide, and a silica-containing inorganic binder are subjected to extrusion molding, thereby producing a catalyst.

The same catalyst as the catalyst 1 which contains zinc oxide and at least one of copper and copper oxide and is explained as to the catalyst prepared by the method (2) described above is exemplified as the catalyst 3.

Examples of the catalyst 4 include catalysts prepared by the method (1).

In the extrusion molding, the catalyst 3 or catalyst 4, the silica-containing inorganic binder, a molding auxiliary and water are kneaded. The resulting kneaded article is extruded, dried and calcined.

(Silica-Containing Inorganic Binder)

Examples of the silica-containing inorganic binder include silica itself; and combinations of silica and inorganic binders such as clay minerals containing as a main component smectite-based swellable clay, e.g., alumina, alumina-silica, activated white earth, bentonite and montmorillonite.

Examples of silica serving as an inorganic binder include powdery silica and colloidal silica. Colloidal silica is a mixture of colloidal silica particles dispersed in water. Alkali-type and ammonium-type colloidal silica are preferably used. Commercially available products such as fumed silica (manufactured by Sigma), Snowtex series (manufactured by Nissan Chemical Industries, Ltd.) and LUDOX colloidal silica (manufactured by Grace Davison) can also be used.

The used amount of silica serving as an inorganic binder is an amount such that the total silica content of the extrusion-molded catalyst is preferably in the range of 0.1% by weight to 25% by weight. The yield of propylene glycol when produced using the catalyst significantly varies depending on whether the total silica content is within the above range or not. The use of the catalyst having a silica content within the above range permits producing propylene glycol in extremely high yield as compared with the case of using a catalyst having a silica content outside the above range.

The catalyst has sufficient strength even if extrusion molding is performed with silica alone used as the silica-containing inorganic binder. To further reinforce the strength of the catalyst, another inorganic binder may be used in combination. The used amount of the silica-containing inorganic binder is usually 3% by weight to 40% by weight, preferably 3% by weight to 35% by weight, and more preferably 3% by weight to 30% by weight with respect to the weight of the catalyst 3 or the catalyst 4.

(Molding Auxiliary)

Examples of the molding auxiliary include substances called thickeners, dispersants, surfactants, deflocculants, humectants or organic binders. Each of these molding auxiliaries often has some characteristics but is called on the basis of one characteristic for convenience. These may be used alone or in combination. The functions of the molding auxiliary are, for example, to adjust the viscosity of the mixture to an extrudable viscosity as well as to uniformly disperse and bond the catalyst 3 or the catalyst 4 and the silica-containing inorganic binder.

Examples of the molding auxiliary include organic compounds, synthetic resins, gum, and natural polymers. For example, at least one selected from methyl cellulose, carboxymethyl cellulose, hydroxyethyl cellulose, polyethylene glycol, polyethylene oxide, polyacrylamide, polypropylene glycol alginate, polyvinylpyrrolidone, polyurethane, xanthan gum, copolymers thereof, and derivatives thereof, may be preferably used. Finally, the molding aid does not remain in the catalyst A because it is burned and/or vaporized in a calcination step subsequent to an extrusion step.

The total amount of the molding auxiliary used is usually 2% by weight to 15% by weight and preferably 2% by weight to 10% by weight with respect to the weight of the catalyst 3 or the catalyst 4.

(Water)

In extrusion molding, the water content is adjusted so as to be usually 20% to 60% and preferably 25% to 55% with respect to the total components (including water) used for the extrusion molding. A water content of less than the above range may result in a kneaded article which has a high viscosity and cannot be subjected to molding process. A water content exceeding the above range may lead to a resulting catalyst having poor crushing strength, so that the catalyst cannot be used as an industrial catalyst.

(Organic Polymer Particles)

In the extrusion molding, to smoothly perform molding operations, organic polymer particles may be added in addition to the silica-containing inorganic binder and water. Examples of the organic polymer particles include silicone rubber, silicone resins, polystyrene, cross-linked polystyrene, polystyrene-based resins, styrene-divinylbenzene copolymer, styrene-acrylic acid copolymer, styrene-acrylic acid ester copolymer, styrene-acrylonitrile copolymer, styrene-methacrylic acid copolymer, styrene-methacrylic acid ester copolymer, styrene-methacrylonitrile copolymer, polyvinyltoluene, polyethylene, polyolefin resins, acrylic resin, cross-linked acrylic resin, ethylene-acrylic acid copolymer, ethylene-acrylic acid ester copolymer, ethylene-acrylonitrile copolymer, ethylene-methacrylic acid copolymer, ethylene-methacrylic acid ester copolymer, ethylene-methacrylonitrile copolymer, polymethyl methacrylate, polyethyl methacrylate, polyglycidyl methacrylate, cross-linked polymethyl methacrylate, polyacrolein, polyglutaraldehyde, polyacrylamide, cross-linked alcoholic resins, phenolic resin, epoxy resins, nylon 6, nylon 66, nylon 11, nylon 12, benzoguanamine resins, melamine resins, melamine-guanamine resin, and poly-n-butyl acrylate.

The total weight of the organic polymer particles used is usually 15% by weight or less and preferably 10% by weight or less with respect to the weight of the catalyst 3 or the catalyst 4. The organic, polymer particles are burned and/or vaporized in the calcination step subsequent to the extrusion step. Thus, finally, they do not remain in the catalyst A.

(Extrusion Molding)

In the extrusion molding, the catalyst A is preferably produced by kneading 100 parts by weight of powders of the catalyst 3 or the catalyst 4, 3 parts by weight to 40 parts by weight of the silica-containing inorganic binder, 2 parts by weight to 15 parts by weight of the molding auxiliary, 20 parts by weight to 60 parts by weight of water, and optionally 15 parts by weight or less of the organic polymer particles, extruding the resulting kneaded article followed by drying and calcination.

The catalyst 3 or the catalyst 4, the raw material of the silica-containing inorganic binder, the molding auxiliary, water, and optionally the organic polymer particles are kneaded to form a kneaded article that can be extruded. The kneading step is performed at room temperature or a temperature equal to or higher than room temperature, producing an appropriate clay-like kneaded article. The kneaded article is molded by using an extruder.

After the kneaded article is extruded, drying is performed. Drying conditions are not particularly limited. The drying is performed in an air or nitrogen atmosphere or under a stream thereof, preferably at 25° C. to 120° C., usually for 1 to 100 hours.

After the drying step, the molded article is calcined at 400° C. to 600° C. for usually 1 to 6 hours in air or in the presence of or under a stream of an oxygen-containing gas. In the calcination step, a method in which a low heating rate is used at first until a predetermined temperature is reached is employed in order not to cause the rapid change of the molded article.

Particles of the catalyst A obtained by extrusion molding may have a spherical shape, a crushed shape, a flat shape, an elliptic shape or the like. The molded catalyst preferably has a diameter of 0.5 to 3 mm.

(Catalyst A Prepared by Extrusion Molding (Method (4)))

The catalyst prepared by the method (4) preferably has a silica content of 0.1% to 25% by weight, more preferably 0.1% to 20% by weight, and particularly preferably 0.4% to 20% by weight with respect to 100% by weight of the catalyst. The yield of propylene glycol when produced using the catalyst significantly varies depending on whether the silica content is within the above range or not. The use of the catalyst having a silica content within the above range permits producing propylene glycol in extremely high yield compared with the case of using a catalyst having a silica content outside the above range.

The content proportion of zinc oxide, silica and the at least one of copper and copper oxide in the catalyst prepared by the method (4) can be adjusted by adjusting the content proportion of respective components in the catalyst 3 or the catalyst 4 used in preparing the catalyst and adjusting the amount of silica in the silica-containing inorganic binder subjected to extrusion molding together with the catalyst 3 or the catalyst 4.

The weight ratio of at least one of copper and copper oxide to silica (at least one of copper and copper oxide:silica) contained in the catalyst prepared by the method (4) is preferably in the range of 1.2:1 to 700:1, more preferably 1.3:1 to 300:1, and particularly preferably 2:1 to 250:1. The yield of propylene glycol when produced using the catalyst significantly varies depending on whether the weight ratio is within the above range or not. The use of the catalyst having a weight ratio within the above range permits producing propylene glycol in extremely high yield as compared with the case of using a catalyst having a weight ratio outside the above range.

The weight ratio of at least one of copper and copper oxide to zinc oxide (at least one of copper and copper oxide:zinc oxide) contained in the catalyst prepared by the method (4) is not particularly limited, but it is usually in the range of 6:1 to 5:90, preferably 5:1 to 10:90, and more preferably 4:1 to 6:35. The use of the catalyst having a weight ratio within the above range allows a catalytic reaction to proceed with a high yield.

The catalyst prepared by the method (4) may contain a fourth component other than zinc oxide, silica and at least one of copper and copper oxide to the extent that the present reaction is not inhibited.

Examples of the component include alkali metals such as sodium, potassium and cesium; alkaline-earth metals such as magnesium and barium; transition metals such as zirconium, manganese, iron, nickel, cobalt, chromium, rhodium, ruthenium, palladium and platinum; the periodic table group 13 elements such as aluminum; and oxides thereof.

The incorporation of the fourth component into the catalyst is expected to improve the persistence of the effect of the catalyst and the stability of the catalyst.

The fourth component may be appropriately contained in the catalyst 3 or the catalyst 4 and/or silica. That is, the fourth component may be contained in one or both of the catalyst 3 or the catalyst 4 and silica.

As described above, the preferred content proportion of zinc oxide, silica and at least one of copper and copper oxide in the catalyst A used in the present invention varies depending on the method for producing the catalyst.

In the catalyst prepared by the method (1), the catalyst is prepared by a coprecipitation method or the like. Thus, zinc oxide, silica and at least one of copper and copper oxide are located at short distances from each other when viewed at the molecular level.

In each of the methods (2) and (3), mixing is simply performed. In the resulting catalyst, thus, zinc oxide, silica and at least one of copper and copper oxide are located at long distances from each other as compared with those of the catalyst prepared by the method (1). Note that zinc oxide and the at least one of copper and copper oxide are located at short distances from each other. This is because the catalyst 1 or 2 containing zinc oxide and at least one of copper and copper oxide is prepared by a known method (e.g., the coprecipitation method, the impregnation method or the kneading method) or is commercially available as explained in the catalyst prepared by the method (2). The commercially available catalysts are also prepared by the known method. In the case where the silica-containing substance or silica-containing catalyst contains at least one of copper and copper oxide in the method (3), silica and the at least one of copper and copper oxide are located at short distances from each other.

With respect to the catalyst prepared by the method (4), simple mixing is not performed, but extrusion molding is performed. In the resulting catalyst, thus, the distances among zinc oxide, silica and at least one of copper and copper oxide are shorter than the distances among the three components in the catalyst prepared by each of the methods (2) and (3) and longer than the distances among the three components in the catalyst prepared by the method (1).

The present invention provides a process for producing propylene glycol by catalytic hydrogenation of glycerol. Regarding the catalyst used in this reaction, copper serves as an active site (copper oxide in the catalyst is reduced into copper during the reaction). Zinc oxide is thought to interact with copper to increase the activity of copper. The inventors believe that silica also interacts with copper to increase the activity of copper. The interactions among copper, zinc oxide, and silica seem to be related to the distances thereof from each other. Thus, the inventors speculate that the catalysts prepared by the above methods (1) to (4) differ from each other in terms of the distances among zinc oxide, silica and at least one of copper and copper oxide, thereby leading to the different preferred proportion of the respective components in these catalysts.

As a general guide, preferred proportion of the three components in the catalyst A used in the present invention regardless of a process for producing the catalyst is described below.

The catalyst A used in the present invention preferably has a silica content of 0.1% to 25% by weight, more preferably 0.2% to 20% by weight, and particularly preferably 0.5% to 20% by weight with respect to 100% by weight of the catalyst A. The use of the catalyst having a silica content within the above range permits producing propylene glycol in extremely high yield.

The weight ratio of at least one of copper and copper oxide to silica (at least one of copper and copper oxide:silica) contained in the catalyst A used in the present invention is preferably in the range of 0.5:1 to 700:1, more preferably 1.0:1 to 500:1, and still more preferably 1.2:1 to 350:1. The use of the catalyst having a weight ratio of at least one of copper and copper oxide to silica within the above range permits producing propylene glycol in extremely high yield.

Further, the weight ratio of at least one of copper and copper oxide to zinc oxide (at least one of copper and copper oxide:zinc oxide) contained in the catalyst A used in the present invention is not particularly limited, but it is usually in the range of 6:1 to 5:90, preferably 5:1 to 10:90, and more preferably 4:1 to 6:35.

[Reaction]

In the production process of the present invention, glycerol is subjected to catalytic hydrogenation in the presence of the catalyst A containing zinc oxide, silica and at least one of copper and copper oxide. The use of the catalyst A containing the three components permits producing propylene glycol from glycerol without vaporization of glycerol. In particular, the present inventors found that the use of the catalyst containing the three components in a specific proportion permitted producing propylene glycol from glycerol with a high yield. Furthermore, the inventors found that, as described above, the preferred proportion of the three components in the catalyst A varied depending on the process for producing the catalyst A.

For a batch reactor, the amount of the catalyst A used is usually 0.1% to 20% by weight and preferably 1% to 10% by weight with respect to 100% by weight of glycerol.

In the production process of the present invention, glycerol is subjected to catalytic hydrogenation to yield propylene glycol. Here, glycerol may be used alone or in the form of an aqueous solution or a solution of an organic solvent. The amount of water or the organic solvent used is not particularly limited, but it is usually in the range of 10% to 90% by weight and preferably 20% to 70% by weight with respect to 100% by weight of glycerol from the viewpoint of volumetric efficiency and the rate of reaction.

Examples of a reactor in which the production process of the present invention is carried out include autoclaves, fixed-bed catalytic reactors, fluidized-bed catalytic reactors and moving-bed catalytic reactors.

In the present invention, a method for charging the catalyst A into a reactor is not particularly limited. For example, in the case of using the catalyst prepared by the method (3), the catalyst 2 containing zinc oxide and at least one of copper and copper oxide is mixed with the silica-containing substance or silica-containing catalyst, and then the mixture may be charged into the reactor. Further, for example, in the case of using the catalyst 2 and the catalyst containing silica and at least one of copper and copper oxide, both of the catalysts may be alternately charged into a fixed-bed reactor in such a manner that one catalyst and the other catalyst form layer(s).

In the case where the catalyst A used in the present invention is used for a reaction, it may be used as it is. Alternatively, before being used for the reaction, the catalyst A may be activated by reduction with hydrogen, thereby completely or partially reduce metal compounds contained in the catalyst A to give a metal. The reduction is typically performed by bringing the catalyst into contact with hydrogen gas at 100° C. to 400° C.

In the case of using the catalyst prepared by the method (3), only the catalyst 2 containing zinc oxide and at least one of copper and copper oxide is subjected to reduction operation, and then the catalyst that has been subjected to reduction operation may be mixed with the silica-containing substance or silica-containing catalyst. Alternatively, a catalyst obtained by mixing the catalyst 2 and the silica-containing substance or silica-containing catalyst may be subjected to reduction operation. Furthermore, each of the catalyst 2 and the catalyst containing silica and at least one of copper and copper oxide may be subjected to reduction operation, and then the resulting two catalysts that have been subjected to reduction operation may be mixed.

The reaction can be usually performed at a reaction temperature of 100° C. to 350° C. and preferably 150° C. to 300° C. in a liquid phase under continuous or batchwise conditions.

Under the continuous or batchwise conditions, the reaction is typically performed at a hydrogen pressure of 1 to 30 MPa and preferably 2 to 20 MPa. The rate of reaction is sufficiently high in this pressure range, thus propylene glycol can be efficiently obtained.

The reaction time is usually 1 to 20 hours.

In the production process of the present invention, propylene glycol can be produced from glycerol without vaporization of glycerol as described above. Of course, glycerol may be vaporized and subjected to catalytic hydrogenation in gaseous phase. Furthermore, a step of removing catalyst poisons from raw material glycerol may be appropriately added before the step of subjecting glycerol to catalytic hydrogenation.

As described above, in the present invention, catalytic hydrogenation of glycerol is performed in the presence of the catalyst A containing zinc oxide, silica and at least one of copper and copper oxide to give propylene glycol. In particular, the use of the catalyst A containing the three components in a specific proportion (preferred proportion of the three components varies depending on the process for producing the catalyst as described above) permits efficiently producing propylene glycol with a high yield. Furthermore, as described above and as will be apparent from examples described below, the specific proportion is significantly important. The use of the catalyst that satisfies the specific proportion permits producing propylene glycol in extremely high yield as compared with that of the case of using a catalyst that does not satisfy the specific proportion.

Specifically, the use of the catalyst A containing the three component in the specific proportion permits the production of propylene glycol at a conversion of glycerol of usually 72% or more and preferably 80% or more and in a yield of usually 70% or more and preferably 75% or more.

EXAMPLES

The present invention will be described in further detail below by examples, but the present invention is not limited thereto. The conversion of glycerol and the yield of propylene glycol were calculated by gas chromatography (with a gas chromatograph, GC-14A from Shimadzu Corporation; column: HP-INNOWAX from Agilent; detector: FID).

Example 1

First, 24 g of glycerol, 6 g of distilled water, 1.0 g of F10G (50% by weight of copper oxide and 50% by weight of zinc oxide) from Nikki Chemical Co., Ltd. and 0.20 g of E35S (67% by weight of copper oxide, 27% by weight of silica and 6% by weight of a binder) from Nikki Chemical Co., Ltd. were weighed and charged into a 100-ml autoclave composed of SUS 316 equipped with an electromagnetic induction rotator stirrer.

After substituting inside of the autoclave with nitrogen (10 MPa×5 times), substitution was carried out with hydrogen (10 MPa×5 times). Finally, the autoclave was filled with hydrogen so as to have an internal pressure of 10 MPa at room temperature, and was then hermetically sealed. The autoclave was heated up to 200° C. to perform catalytic hydrogenation reaction while stirring the reaction solution containing the catalyst in the autoclave at a stirring rate of 450 rpm. The heating was stopped after 12 hours. The autoclave was left to natural cooling. The inside the autoclave was substituted with nitrogen after the temperature inside the autoclave reached 30° C. or lower, and then the autoclave was opened. The contents were filtrated to remove the catalyst. Analysis of the resulting reaction solution by gas chromatography showed that the conversion of glycerol was 91.1% and the yield of propylene glycol was 86.0%.

Examples 2 to 9 and Comparative Examples 1 and 2

In each of Examples 2 to 9 and Comparative Examples 1 and 2, the reaction was performed in the same manner as in Example 1, except that the amounts of F10G and E35S used were changed as shown in Table 1. Table 1 shows the results together with that of Example 1.

Table 1 shows that in the case where the catalyst (catalyst prepared by the method (3)) used in the present reaction had a silica content of 0.1% to 10% by weight, propylene glycol was able to be produced from glycerol in extremely high yield as compared with the case where the catalyst had a silica content of 13.5% by weight (Example 7).

Preparation Example 1a

Preparation of Catalyst with Copper Oxide:Zinc Oxide=30:70 (Weight Ratio) (Hereinafter, Abbreviated as "Catalyst 1a")

Copper nitrate trihydrate (18.2 g) and zinc nitrate hexahydrate (51.2 g) were dissolved in distilled water to prepare 400 ml of an aqueous solution (hereinafter, the aqueous solution is abbreviated as an "aqueous solution A"). Meanwhile, anhydrous sodium carbonate (34.1 g) was dissolved in distilled water to prepare 400 ml of an aqueous solution (hereinafter, the aqueous solution is abbreviated as an "aqueous solution B").

Next, each of the aqueous solution A and the aqueous solution B was simultaneously added dropwise to 150 ml of distilled water under vigorous stirring to perform a reaction. The resulting precipitate was filtered off and subjected to sludging with distilled water. The resulting solid was dried at 110° C. for 3 hours and then calcined at 400° C. for 3 hours in air.

Elementary analysis value of the resulting solid showed that the solid was a catalyst (catalyst 1a) having a ratio of copper oxide:zinc oxide of 30:70 (weight ratio).

Preparation Examples 1b to f

Catalysts 1b to 1f shown in Table 2 were prepared in the same manner as in Preparation Example 1a, except that the amounts of copper nitrate trihydrate and zinc nitrate hexahydrate used were changed.

TABLE 1

| | F10G | E35S | Conversion of Glycerol (%) | Yield of propylene glycol (%) | Copper oxide/silica weight ratio | Copper oxide/zinc oxide weight ratio | Silica content (wt %) |
|---|---|---|---|---|---|---|---|
| Example 1 | 1.000 g | 0.200 g | 91.1 | 86.0 | 11.7 | 1.3 | 4.5 |
| Example 2 | 1.090 g | 0.110 g | 92.6 | 88.3 | 20.8 | 1.1 | 2.5 |
| Example 3 | 1.200 g | 0.240 g | 98.5 | 93.9 | 11.7 | 1.3 | 4.5 |
| Example 4 | 0.978 g | 0.222 g | 89.9 | 85.4 | 10.6 | 1.3 | 5 |
| Example 5 | 0.923 g | 0.277 g | 89.6 | 82.6 | 8.7 | 1.4 | 6.2 |
| Example 6 | 0.800 g | 0.400 g | 73.5 | 70.3 | 6.2 | 1.7 | 9 |
| Example 7 | 0.600 g | 0.600 g | 27.0 | 26.0 | 4.3 | 2.3 | 13.5 |
| Example 8 | 1.195 g | 0.005 g | 87.6 | 83.2 | 445 | 1 | 0.1 |
| Example 9 | 1.178 g | 0.022 g | 89.6 | 85.2 | 102 | 1 | 0.5 |
| Comparative Example 1 | 1.200 g | none | 86.4 | 81.5 | | | |
| Comparative Example 2 | none | 1.200 g | 36.6 | 30.1 | | | |

Remark)
Silica content was calculated using {amount of silica/(F10G + E35S)} × 100.

TABLE 2

| | Catalyst name | Copper oxide:zinc oxide weight ratio |
|---|---|---|
| Preparation example 1a | Catalyst 1a | 30:70 |
| Preparation example 1b | Catalyst 1b | 15:85 |
| Preparation example 1c | Catalyst 1c | 7.5:92.5 |
| Preparation example 1d | Catalyst 1d | 50:50 |
| Preparation example 1e | Catalyst 1e | 60:40 |
| Preparation example 1f | Catalyst 1f | 70:30 |

Examples 10 to 17 and Comparative Examples 3 to 8

In each of Examples 10 to 17 and Comparative Examples 3 to 8, the reaction was performed in the same manner as in Example 1, except that the type and amount of catalyst used were changed as shown in Table 3. Table 3 shows the results.

From Table 3, comparisons between the examples and the comparative examples that use the same types of copper oxide/zinc oxide catalysts (e.g., between Example 10 and Comparative Example 3, between Example 11 and Comparative Example 4, and between Example 12 and Comparative Example 5) show that, in the cases where the catalysts (catalysts prepared by the method (3)) used in the present invention each had a silica content of 0.1% to 10% by weight, propylene glycol was able to be produced from glycerol in extremely high yields as compared with the case of using the copper oxide/zinc oxide catalysts (Comparative Examples).

Example 18

The reaction was performed in the same manner as in Example 3, except that 0.007 g of silica (CARiACT Q6 from Fuji Silysia Chemical Ltd.) was used instead of E35S in Example 3. The conversion of glycerol was 99.1%, and the yield of propylene glycol was 96.1%.

Examples 19 to 28

In each of Examples 19 to 28, the reaction was performed in the same manner as in Example 18, except that the type and amount of catalyst and the amount of CARiACT Q6 used were changed as shown in Table 4. Table 4 shows the results together with that of Example 18.

TABLE 3

| | Copper oxide/zinc oxide catalyst | | | Conversion of Glycerol (%) | Yield of propylene glycol (%) | Copper oxide/silica weight ratio | Copper oxide/zinc oxide weight ratio | Silica content (wt %) |
|---|---|---|---|---|---|---|---|---|
| | Catalyst | Used amount | E35S | | | | | |
| Example 10 | Catalyst 1a | 1.090 g | 0.110 g | 87.9 | 83.6 | 13.5 | 0.53 | 2.5 |
| Example 11 | Catalyst 1b | 1.090 g | 0.110 g | 82.9 | 78.8 | 12.1 | 0.39 | 2.5 |
| Example 12 | Catalyst 1c | 1.090 g | 0.110 g | 74.1 | 70.4 | 5.2 | 0.15 | 2.5 |
| Example 13 | Catalyst 1d | 1.090 g | 0.110 g | 93.5 | 89.9 | 20.8 | 1.1 | 2.5 |
| Example 14 | Catalyst 1e | 1.090 g | 0.110 g | 92.3 | 87.9 | 24.5 | 1.7 | 2.5 |
| Example 15 | Catalyst 1f | 1.090 g | 0.110 g | 90.2 | 85.8 | 28.2 | 2.6 | 2.5 |
| Example 16 | Catalyst 1a | 0.978 g | 0.222 g | 84.0 | 79.8 | 7.4 | 0.65 | 5 |
| Example 17 | Catalyst 1a | 1.178 g | 0.022 g | 83.5 | 72.5 | 62 | 0.45 | 0.5 |
| Comparative Example 3 | Catalyst 1a | 1.200 g | None | 80.1 | 76.7 | | | |
| Comparative Example 4 | Catalyst 1b | 1.200 g | None | 76.2 | 78.8 | | | |
| Comparative Example 5 | Catalyst 1c | 1.200 g | None | 71.6 | 66.2 | | | |
| Comparative Example 6 | Catalyst 1d | 1.200 g | None | 85.5 | 81.7 | | | |
| Comparative Example 7 | Catalyst 1e | 1.200 g | None | 84.9 | 80.8 | | | |
| Comparative Example 8 | Catalyst 1f | 1.200 g | None | 84.3 | 80.2 | | | |

Remark)
Silica content was calculated using {amount of silica/(catalyst + E35S)} × 100.

TABLE 4

| | Copper oxide/zinc oxide catalyst | | | Conversion of Glycerol (%) | Yield of propylene glycol (%) | Copper oxide/silica weight ratio | Copper oxide/zinc oxide weight ratio | Silica content (wt %) |
|---|---|---|---|---|---|---|---|---|
| | Catalyst | Used amount | CARiACT Q6 | | | | | |
| Example 18 | F10G | 1.200 g | 0.007 g | 99.1 | 96.1 | 85.7 | 1 | 0.58 |
| Example 19 | F10G | 1.200 g | 0.033 g | 98.2 | 95.7 | 18.2 | 1 | 2.67 |
| Example 20 | F10G | 1.200 g | 0.065 g | 15.1 | 14.3 | 9.2 | 1 | 5.14 |
| Example 21 | F10G | 1.200 g | 0.240 g | 10.7 | 4.9 | 2.5 | 1 | 16.7 |
| Example 22 | F10G | 1.200 g | 0.001 g | 86.9 | 82.6 | 600 | 1 | 0.1 |
| Example 23 | F10G | 1.200 g | 0.002 g | 93.4 | 88.9 | 300 | 1 | 0.2 |
| Example 24 | F10G | 1.200 g | 0.050 g | 87.3 | 83.1 | 12 | 1 | 4 |
| Example 25 | Catalyst 1a | 1.200 g | 0.033 g | 93.6 | 89.5 | 10.9 | 0.43 | 2.67 |
| Example 26 | Catalyst 1c | 1.200 g | 0.033 g | 76.2 | 72.6 | 2.7 | 0.08 | 2.67 |

TABLE 4-continued

| | Copper oxide/zinc oxide catalyst | | | | Copper | Copper | Silica |
| | Catalyst | Used amount | CARiACT Q6 | Conversion of Glycerol (%) | Yield of propylene glycol (%) | oxide/silica weight ratio | oxide/zinc oxide weight ratio | content (wt %) |
|---|---|---|---|---|---|---|---|---|
| Example 27 | Catalyst 1d | 1.200 g | 0.033 g | 95.3 | 91.2 | 18.2 | 1 | 2.67 |
| Example 28 | Catalyst 1e | 1.200 g | 0.033 g | 91.2 | 87.8 | 21.8 | 1.5 | 2.67 |

Remark)
Silica content was calculated using {amount of silica/(catalyst + CARiACT Q6)} × 100.

Table 4 shows that, as compared with Examples 20 and 21 in which the silica content of each of the catalysts (catalysts prepared by the method (2)) used in the present invention was outside the range of 0.1% to 4.5% by weight, propylene glycol was able to be produced from glycerol in extremely high yields in the other examples in which the silica content of each of the catalysts was within the above range.

Preparation Example 2a

Preparation of Catalyst with Copper Oxide:Zinc Oxide:Silica=50:40:10 (% by Weight) (Hereinafter, abbreviated as "catalyst 2a")

Copper nitrate trihydrate (38.0 g), zinc nitrate hexahydrate (36.6 g) and 12.5 g of colloidal silica (Snowtex O from Nissan Chemical Industries, Ltd.; silica concentration: 20% by weight; water: 80% by weight) were dissolved in distilled water to prepare 500 ml of an aqueous solution (hereinafter, abbreviated as an "aqueous solution E"). Meanwhile, an aqueous solution of anhydrous sodium carbonate (32.7 g) was dissolved in distilled water to prepare 500 ml of an aqueous solution (hereinafter, abbreviated as an "aqueous solution F").

Next, each of the aqueous solution E and the aqueous solution F was simultaneously added dropwise to 300 ml of distilled water under vigorous stirring to perform a reaction. The resulting precipitate was filtered off and subjected to sludging with distilled water. The resulting solid was dried at 110° C. for 3 hours and then calcined at 400° C. for 3 hours in air.

Elementary analysis value of the resulting solid showed that the solid was a catalyst (catalyst 2a) having a ratio of copper oxide:zinc oxide:silica of 50:40:10 (% by weight).

Preparation Examples 2b to 2p

The following copper oxide:zinc oxide:silica catalysts (catalysts 2b to 2p) were prepared in the same manner as in Preparation Example 2a, except that the amounts of copper nitrate trihydrate, zinc nitrate hexahydrate and colloidal silica used were changed.

TABLE 5

| | Catalyst name | Copper oxide:zinc oxide:silica weight ratio | Copper oxide/silica weight ratio | Copper oxide/zinc oxide weight ratio | Silica content (wt %) |
|---|---|---|---|---|---|
| Preparation example 2a | Catalyst 2a | 50:40:10 | 5 | 1.25 | 10 |
| Preparation example 2b | Catalyst 2b | 50:45:5 | 10 | 1.11 | 5 |
| Preparation example 2c | Catalyst 2c | 50:49:1 | 50 | 1 | 1 |
| Preparation example 2d | Catalyst 2d | 50:49.5:0.5 | 100 | 1 | 0.5 |
| Preparation example 2e | Catalyst 2e | 50:49.9:0.1 | 500 | 1 | 0.1 |
| Preparation example 2f | Catalyst 2f | 50:35:15 | 3.33 | 1.43 | 15 |
| Preparation example 2g | Catalyst 2g | 50:30:20 | 2.5 | 1.67 | 20 |
| Preparation example 2h | Catalyst 2h | 50:20:30 | 1.67 | 2.5 | 30 |
| Preparation example 2i | Catalyst 2i | 30:60:10 | 3 | 0.5 | 10 |
| Preparation example 2j | Catalyst 2j | 15:75:10 | 1.5 | 0.2 | 10 |
| Preparation example 2k | Catalyst 2k | 7.5:82.5:10 | 0.75 | 0.09 | 10 |
| Preparation example 2m | Catalyst 2m | 60:30:10 | 6 | 2 | 10 |
| Preparation example 2n | Catalyst 2n | 70:20:10 | 7 | 3.5 | 10 |
| Preparation example 2p | Catalyst 2p | 45:45:10 | 4.5 | 1 | 10 |

Remark)
Silica content was calculated using (amount of silica/catalyst) × 100.

Examples 29 to 42

The reaction was performed in the same manner as in Example 1, except that each of the catalysts 2a to 2p was used as a catalyst for use in the reaction in an amount of 1.200 g. Table 6 shows the results.

TABLE 6

| | Catalyst | Conversion of Glycerol (%) | Yield of propylene glycol (%) | Copper oxide/silica weight ratio | Copper oxide/zinc oxide weight ratio | Silica content (wt %) |
|---|---|---|---|---|---|---|
| Example 29 | Catalyst 2a | 97.4 | 93.2 | 5 | 1.25 | 10 |
| Example 30 | Catalyst 2b | 99.5 | 96.1 | 10 | 1.11 | 5 |
| Example 31 | Catalyst 2c | 95.2 | 90.4 | 50 | 1 | 1 |
| Example 32 | Catalyst 2d | 91.6 | 87.2 | 100 | 1 | 0.5 |
| Example 33 | Catalyst 2e | 87.3 | 82.9 | 500 | 1 | 0.1 |
| Example 34 | Catalyst 2f | 83.9 | 82.1 | 3.33 | 1.43 | 15 |
| Example 35 | Catalyst 2g | 77.6 | 74.1 | 2.5 | 1.67 | 20 |
| Example 36 | Catalyst 2h | 29.1 | 6.6 | 1.67 | 2.5 | 30 |
| Example 37 | Catalyst 2i | 99.2 | 92.7 | 3 | 0.5 | 10 |
| Example 38 | Catalyst 2j | 98.5 | 93.2 | 1.5 | 0.2 | 10 |
| Example 39 | Catalyst 2k | 75.8 | 72.8 | 0.75 | 0.09 | 10 |
| Example 40 | Catalyst 2m | 96.9 | 89.1 | 6 | 2 | 10 |
| Example 41 | Catalyst 2n | 89.8 | 86.1 | 7 | 3.5 | 10 |
| Example 42 | Catalyst 2p | 98.7 | 91.2 | 4.5 | 1 | 10 |

Preparation Example 3a

Preparation of Catalyst with Copper Oxide:Zinc Oxide:Silica=45:45:10 (% by Weight) (Hereinafter, Abbreviated as "Catalyst 3a")

5.6 g of colloidal silica (Snowtex S from Nissan Chemical Industries, Ltd.; silica concentration: 20% by weight; water: 80% by weight), 0.4 g of xanthan gum, and 5.6 g of distilled water (10.1 g in total with water derived from Snowtex S) were added to 10 g of the catalyst having a ratio of copper oxide:zinc oxide of 50:50 prepared in Preparation Example 1d and well mixed. The resulting mixture was extruded through a nozzle with a diameter of 3 mm, dried at 110° C. for 3 hours, and calcined at 400° C. for 3 hours in air.

Elementary analysis value of the resulting solid showed that the solid was a catalyst (catalyst 3a) having a ratio of copper oxide:zinc oxide:silica of 45:45:10 (% by weight). To eliminate the difference between the resulting catalyst and the catalyst used in each of Examples up to 42 in terms of the contact efficiency (contact area) with glycerol and hydrogen, the catalyst 3a was pulverized and then used in a test of Example 43.

Preparation Examples 3b to 3u

In Preparation Examples 3b to 3u, copper oxide:zinc oxide: silica catalysts (catalysts 3b to 3u) shown in Table 7 below were prepared in the same manner as in Preparation Example 3a, except that the types of catalysts mixed with colloidal silica, xanthan gum, and distilled water, the amounts of colloidal silica used and the amounts of distilled water used were changed as shown in Table 7 below. These catalysts were also pulverized and then used in respective Examples 44 to 61.

TABLE 7

| | | Raw material for catalyst | | | Catalyst after molding | | | |
|---|---|---|---|---|---|---|---|---|
| | Catalyst name | Copper oxide:zinc oxide weight ratio | Amount of colloidal silica used | Amount of distilled water used | Copper oxide:zinc oxide:silica weight ratio | Copper oxide/silica weight ratio | Copper oxide/zinc oxide weight ratio | Silica content (wt %) |
| Preparation example 3a | Catalyst 3a | 50:50:0 | 5.6 g | 5.6 g | 45:45:10 | 4.5 | 1 | 10 |
| Preparation example 3b | Catalyst 3b | 50:50:0 | 8.8 g | 3.1 g | 42.5:42.5:15 | 2.83 | 1 | 15 |
| Preparation example 3c | Catalyst 3c | 50:50:0 | 12.5 g | 0.5 g | 40:40:20 | 2 | 1 | 20 |
| Preparation example 3d | Catalyst 3d | 50:50:0 | 16.7 g | 0 g | 37.5:37.5:25 | 1.5 | 1 | 25 |
| Preparation example 3e | Catalyst 3e | 50:50:0 | 21.4 g | 0 g | 35:35:30 | 1.17 | 1 | 30 |
| Preparation example 3f | Catalyst 3f | 50:50:0 | 2.6 g | 8.0 g | 47.5:47.5:5 | 9.6 | 1 | 5 |
| Preparation example 3g | Catalyst 3g | 50:50:0 | 1.5 g | 8.8 g | 48.5:48.5:3 | 16.7 | 1 | 3 |
| Preparation example 3h | Catalyst 3h | 50:50:0 | 0.5 g | 9.7 g | 49.5:49.5:1 | 50 | 1 | 1 |
| Preparation example 3i | Catalyst 3i | 50:50:0 | 0.2 g | 10.0 g | 49.8:49.8:0.4 | 125 | 1 | 0.4 |
| Preparation example 3j | Catalyst 3j | 50:50:0 | 0.05 g | 10.1 g | 50:50:0.1 | 500 | 1 | 0.1 |
| Preparation example 3k | Catalyst 3k | 70:30:0 | 5.6 g | 5.6 g | 63:27:10 | 6.3 | 2.33 | 10 |
| Preparation example 3m | Catalyst 3m | 60:40:0 | 5.6 g | 5.6 g | 54:36:10 | 5.4 | 1.5 | 10 |
| Preparation example 3n | Catalyst 3n | 30:70:0 | 5.6 g | 5.6 g | 27:63:10 | 2.7 | 0.43 | 10 |
| Preparation example 3p | Catalyst 3p | 15:85:0 | 5.6 g | 5.6 g | 13.5:76.5:10 | 1.34 | 0.18 | 10 |
| Preparation example 3q | Catalyst 3q | 55:45:0 | 5.6 g | 5.6 g | 49.5:40.5:10 | 4.9 | 1.22 | 10 |
| Preparation example 3r | Catalyst 3r | 50:48:2 | 4.4 g | 6.5 g | 46:44:10 | 5.7 | 1 | 10 |
| Preparation example 3s | Catalyst 3s | 50:48:2 | 7.6 g | 3.9 g | 43:42:15 | 3.3 | 1 | 15 |
| Preparation example 3t | Catalyst 3t | 50:48:2 | 11.3 g | 1.1 g | 41:39:20 | 2.2 | 1.1 | 20 |
| Preparation example 3u | Catalyst 3u | 50:45:5 | 2.8 g | 7.8 g | 47:43:10 | 8.9 | 1.1 | 10 |

Examples 43 to 61

The reaction was performed in the same manner as in Example 1, except that each of the catalysts 3a to 3u was used as a catalyst used in an amount of 1.200 g. Table 8 shows the results.

TABLE 8

| | Catalyst | Conversion of Glycerol (%) | Yield of propylene glycol (%) | Copper oxide/silica weight ratio | Copper oxide/zinc oxide weight ratio | Silica content (wt %) |
|---|---|---|---|---|---|---|
| Example 43 | Catalyst 3a | 97.5 | 94.6 | 4.5 | 1 | 10 |
| Example 44 | Catalyst 3b | 92.6 | 89.3 | 2.83 | 1 | 15 |
| Example 45 | Catalyst 3c | 87.4 | 84.3 | 2 | 1 | 20 |
| Example 46 | Catalyst 3d | 80.8 | 77.4 | 1.5 | 1 | 25 |
| Example 47 | Catalyst 3e | 9.7 | 8.6 | 1.17 | 1 | 30 |
| Example 48 | Catalyst 3f | 95.9 | 92.1 | 9.6 | 1 | 5 |
| Example 49 | Catalyst 3g | 94.5 | 91.9 | 16.7 | 1 | 3 |
| Example 50 | Catalyst 3h | 94.0 | 90.6 | 50 | 1 | 1 |
| Example 51 | Catalyst 3i | 93.6 | 88.9 | 125 | 1 | 0.4 |
| Example 52 | Catalyst 3j | 88.2 | 83.7 | 500 | 1 | 0.1 |
| Example 53 | Catalyst 3k | 93.4 | 88.4 | 6.3 | 2.33 | 10 |
| Example 54 | Catalyst 3m | 95.3 | 91.2 | 5.4 | 1.5 | 10 |
| Example 55 | Catalyst 3n | 88.2 | 84.8 | 2.7 | 0.43 | 10 |
| Example 56 | Catalyst 3p | 81.9 | 78.7 | 1.34 | 0.18 | 10 |
| Example 57 | Catalyst 3q | 96.1 | 92.8 | 4.9 | 1.22 | 10 |
| Example 58 | Catalyst 3r | 99.2 | 96.0 | 5.7 | 1 | 10 |
| Example 59 | Catalyst 3s | 93.6 | 90.1 | 3.3 | 1 | 15 |
| Example 60 | Catalyst 3t | 88.0 | 84.7 | 2.2 | 1.1 | 20 |
| Example 61 | Catalyst 3u | 99.0 | 95.8 | 8.9 | 1.1 | 10 |

The invention claimed is:

1. A process for producing propylene glycol comprising a step of subjecting glycerol to catalytic hydrogenation in the presence of a catalyst A containing zinc oxide, silica, and at least one of copper and copper oxide.

2. The process for producing propylene glycol according to claim 1, wherein the catalyst A has a silica content of 0.1% to 25% by weight with respect to 100% by weight of the catalyst A.

3. The process for producing propylene glycol according to claim 1, wherein the weight ratio of the at least one of copper and copper oxide to silica (at least one of copper and copper oxide:silica) in the catalyst A is in the range of 0.5:1 to 700:1.

4. The process for producing propylene glycol according to claim 1, wherein the weight ratio of the at least one of copper and copper oxide to zinc oxide (at least one of copper and copper oxide:zinc oxide) in the catalyst A is in the range of 6:1 to 5:90.

5. The process for producing propylene glycol according to claim 1, wherein the catalyst A is prepared by a coprecipitation method or an impregnation method, and
the catalyst A has a silica content of 0.1% to 25% by weight with respect to 100% by weight of the catalyst A.

6. The process for producing propylene glycol according to claim 5, wherein the weight ratio of the at least one of copper and copper oxide to silica (at least one of copper and copper oxide:silica) in the catalyst A is in the range of 0.5:1 to 700:1.

7. The process for producing propylene glycol according to claim 5, wherein the weight ratio of the at least one of copper and copper oxide to zinc oxide (at least one of copper and copper oxide:zinc oxide) in the catalyst A is in the range of 6:1 to 5:90.

8. The process for producing propylene glycol according to claim 1, wherein the catalyst A is prepared by mixing
a catalyst containing zinc oxide and at least one of copper and copper oxide, and
silica,
and wherein the catalyst A has a silica content of 0.1% to 4.5% by weight with respect to 100% by weight of the catalyst A.

9. The process for producing propylene glycol according to claim 8, wherein the weight ratio of the at least one of copper and copper oxide to silica (at least one of copper and copper oxide:silica) in the catalyst A is in the range of 1.5:1 to 700:1.

10. The process for producing propylene glycol according to claim 8, wherein the weight ratio of the at least one of copper and copper oxide to zinc oxide (at least one of copper and copper oxide:zinc oxide) in the catalyst A is in the range of 6:1 to 5:90.

11. The process for producing propylene glycol according to claim 1, wherein the catalyst A is prepared by mixing
a catalyst containing zinc oxide and at least one of copper and copper oxide, and
a silica-containing substance or a silica-containing catalyst,
and wherein the catalyst A has a silica content of 0.1% to 10% by weight with respect to 100% by weight of the catalyst A.

12. The process for producing propylene glycol according to claim 11, wherein the weight ratio of the at least one of copper and copper oxide to silica (at least one of copper and copper oxide:silica) in the catalyst A is in the range of 5:1 to 700:1.

13. The process for producing propylene glycol according to claim 11, wherein the weight ratio of the at least one of copper and copper oxide to zinc oxide (at least one of copper and copper oxide:zinc oxide) in the catalyst A is in the range of 6:1 to 5:90.

14. The process for producing propylene glycol according to claim 1, wherein the catalyst A is prepared by extrusion molding of
a catalyst containing zinc oxide and at least one of copper and copper oxide, or a catalyst containing zinc oxide, silica, and at least one of copper and copper oxide, and
a silica-containing inorganic binder,
and wherein the catalyst A has a silica content of 0.1% to 25% by weight with respect to 100% by weight of the catalyst A.

15. The process for producing propylene glycol according to claim 14, wherein the weight ratio of the at least one of copper and copper oxide to silica (at least one of copper and copper oxide:silica) in the catalyst A is in the range of 1.2:1 to 700:1.

16. The process for producing propylene glycol according to claim 14, wherein the weight ratio of the at least one of copper and copper oxide to zinc oxide (at least one of copper and copper oxide:zinc oxide) in the catalyst A is in the range of 6:1 to 5:90.

17. The process for producing propylene glycol according to claim 2, wherein the weight ratio of the at least one of copper and copper oxide to silica (at least one of copper and copper oxide:silica) in the catalyst A is in the range of 0.5:1 to 700:1.

18. The process for producing propylene glycol according to claim 2, wherein the weight ratio of the at least one of copper and copper oxide to zinc oxide (at least one of copper and copper oxide:zinc oxide) in the catalyst A is in the range of 6:1 to 5:90.

19. The process for producing propylene glycol according to claim 3, wherein the weight ratio of the at least one of copper and copper oxide to zinc oxide (at least one of copper and copper oxide:zinc oxide) in the catalyst A is in the range of 6:1 to 5:90.

20. The process for producing propylene glycol according to claim 6, wherein the weight ratio of the at least one of copper and copper oxide to zinc oxide (at least one of copper and copper oxide:zinc oxide) in the catalyst A is in the range of 6:1 to 5:90.

* * * * *